US009265806B2

(12) United States Patent
Yang et al.

(10) Patent No.: US 9,265,806 B2
(45) Date of Patent: *Feb. 23, 2016

(54) COMPOSITION FOR PREVENTING OR TREATING DEMENTIA COMPRISING EXTRACTS OF MONSONIA SPECIES

(71) Applicants: KOREA INSTITUTE OF SCIENCE AND TECHNOLOGY, Seoul (KR); COUNCIL FOR SCIENTIFIC AND INDUSTRIAL RESEARCH (CSIR), Pretoria (ZA)

(72) Inventors: Hyun Ok Yang, Seoul (KR); Sung-Kwon Chung, Seoul (KR); Hak Cheol Kwon, Seoul (KR); Jin Wook Cha, Incheon (KR); Vinesh Jaichand Maharaj, Pretoria (ZA); Rudzani Nthambeleni, Pretoria (ZA); Dashnie Naidoo, Pretoria (ZA); Young-Joo Kim, Seoul (KR); Jungyeob Ham, Gangneung (KR); Jeremiah Senabe, Pretoria (ZA); Gerda Fouche, Pretoria (ZA); Eric Khorombi, Pretoria (ZA); Joon Ki Kim, Gunpo (KR)

(73) Assignees: KOREA INSTITUTE OF SCIENCE AND TECHNOLOGY, Seoul (KR); CSIR, Gauteng (ZA)

( * ) Notice: Subject to any disclaimer, the term of this patent is extended or adjusted under 35 U.S.C. 154(b) by 23 days.

This patent is subject to a terminal disclaimer.

(21) Appl. No.: 14/038,378

(22) Filed: Sep. 26, 2013

(65) Prior Publication Data
US 2014/0087008 A1 Mar. 27, 2014

(51) Int. Cl.
*A01N 65/00* (2009.01)
*A61K 36/185* (2006.01)
*A23L 1/30* (2006.01)
*A23L 2/52* (2006.01)

(52) U.S. Cl.
CPC .............. *A61K 36/185* (2013.01); *A23L 1/3002* (2013.01); *A23L 2/52* (2013.01); *A61K 2236/39* (2013.01)

(58) Field of Classification Search
CPC ........................................................ A61K 36/00
USPC ........................................................ 424/725
See application file for complete search history.

(56) References Cited

U.S. PATENT DOCUMENTS 7,179,484 B2   2/2007  Singh
2007/0155771 A1   7/2007  Rubinsztein et al.
2009/0202662 A1*  8/2009  Fouche et al. ................. 424/725

FOREIGN PATENT DOCUMENTS

JP      2008-534582      8/2008
KR      10-0404719      11/2003
WO      WO 2007/138531 A2  12/2007

OTHER PUBLICATIONS

Katsura Munakata et al., "Justicidin A and B, the Fish-Killing Components of *Justicia Hayatai* Var. *Decumbens*", Tetrahedron Letters; No. 47, 1965, pp. 4167-4170.
CAS RN: 25001-57-4 (entered Nov. 16, 1984).
Chien-Chih Chen et al., "Antiplatelet Arylnaphthalide Lignans from *Justicia procumbens*" J. Nat. Prod., No. 59, 1996, pp. 1149-1150.
Antonio C. Siani et al,. "5-Methoxyjusticidin A, a New Arylnaphthalene Lignan from *Protium Unifoliolatum*" J. Nat. Prod., No. 61, 1998, pp. 796-797.
Korean Patent Abstracts, Publication No. 10-2002-0046356, published Jun. 21, 2002.
Front page and Abstract of International Publication No. WO 2006/104369, published Oct. 5, 2006, corresponding to Japanese Publication No. 2008-534582.
Peer-Hendrik Kuhn et al., "ADAM10 is the Physiologically Relevant, Constitutive α-Secretase of the Amyloid Precursor Protein in Primary Neurons", The EMBO Journal, vol. 29, No. 17, 2010, pp. 3020-3032.
Su et al., "Justicidin A inhibits AKT/mTOR and activates type III PI3K/beclin 1 signaling pathways leading to autophagy of human colorectal cancer cells," The Journal of the Federation of American Societies for Experimental Biology, Apr. 2010.
Extended European Search Report mailed Dec. 3, 2013 in Application No. 13185993.6.
U.S. Office Action mailed on Mar. 17, 2014 in U.S. Appl. No. 14/036,810.
U.S. Office Action mailed on Sep. 25, 2014 in U.S. Appl. No. 14/036,810.
U.S. Office Action mailed on Jan. 28, 2015 in U.S. Appl. No. 14/036,810.
U.S. Appl. No. 14/036,810, filed Sep. 25, 2013, Hyun Ok Yang et al., (1) Korea Institute of Science and Technology (2) CSIR.
T. A. Henry et al., "Observations on Reputed Dysentery Remedies", Transactions of the Royal Society of Tropical Medicine and Hygiene, Elsevier, GB, vol. 17, No. 6, Dec. 13, 1923, pp. 378-385.
"Revista Brasileira de Farmacognosia", Brazillian Journal of Pharmacognosy, Elsevier, p. 1.
Alphonse Probst et al., "Alzheimer's Disease: A Description of the Structural Lesions", Brain Pathology, vol. 1, 1991, pp. 229-239.
Lars H. Breimer et al., "Alzheimer Amyloid Aspects", Scientific Correspondence, Nature vol. 326, Apr. 23, 1987, pp. 749-750.

(Continued)

*Primary Examiner* — Michael Meller
(74) *Attorney, Agent, or Firm* — Staas & Halsey LLP

(57) ABSTRACT

A pharmaceutical composition and a food composition including extracts of *Monsonia* sp. for treating dementia, which compositions inhibit the formation of β-amyloid, and a method of preparing the extracts.

10 Claims, 4 Drawing Sheets

(56) References Cited

OTHER PUBLICATIONS

Robert Vassar et al., "Aβ-Generating Enzymes: Recent Advances in β-and γ-Secretase Reesearch" Neuron, vol. 27, Sep. 2000, pp. 419-422.

Dennis J. Selkoe, "Alzheimer's Disease is a Synaptic Failure", Science, vol. 298, Oct. 25, 2002, pp. 789-791 with cover page.

H. M. Burkill, "The Useful Plants of West Tropical Africa", Royal Botanic Gardens Kew, vol. 2, 1994, p. 167 with cover pages.

Margaret Roberts, "Indigenous Healing Plants", Southern Book Publishers, 1990, pp. 81-82 with cover pages.

Ichikawa, "AFlora The Database of Plant Utilization in Africa", The Center for African Area Studies, Kyoto University, p. 1.

Extended European Search Report mailed Nov. 13, 2013 in corresponding European Application No. 13185164.4.

Notice of Allowance in co-pending U.S. Appl. No. 14/036,810 issued Aug. 20, 2015.

* cited by examiner

COMPOSITION FOR PREVENTING OR TREATING DEMENTIA COMPRISING EXTRACTS OF MONSONIA SPECIES

CROSS-REFERENCE TO RELATED APPLICATIONS

This application claims the benefit of Korean Patent Application No. 10-2012-0107323, filed on Sep. 26, 2012, in the Korean Intellectual Property Office, the entire disclosure of which is incorporated herein by reference.

BACKGROUND OF THE INVENTION

1. Field of the Invention

The present invention relates to a composition or a method for preventing treating, improving and/or ameliorating a disease associated with β-amyloid in brain which is at least one selected from dementia, memory impairment and memory, by using.

2. Description of the Related Art

Generally, dementia is a symptom showing remarkably decreased brain functions such as the abilities of memory, thinking, understanding, calculating, learning, language, and judgment, in which the brain normal cell is damaged due to various reasons.

In particular, Alzheimer's disease is an important disease of senile dementia, and is mainly caused by the accumulation of β-amyloid in the brain and its neurotoxicity (Probst A. et al., Brain Pathol., 1:229-239, 1991). It has been reported that β-amyloid makes the protein plaque in brain, thereby causing the occurrence of Alzheimer's disease (Breimer L H, et al. Nature, 326: 749-750, 1987).

The β-amyloid is prepared by reacting amyloid precursor protein (APP) with β-secretase (BACE1) and gamma-secretase sequentially (Vassa and Citron, Neuron 27, 419-422, 2000). β-amyloid is largely classified into two types; Aβ40 of 40 amino acids and Aβ42 of 42 amino acids. β-amyloid is predominantly Aβ40 but a relatively small amount of Aβ42 makes plaque formation easily and thus is considered as a factor causing the disease (Selkoe, Science 298: 789-891, 2002).

The representative drugs for treating dementia which are commercially available are tacrine (Cognex, 1994) and donepezil (Aricept, 1996) used after U.S. FDA approval. The mechanism of drugs to prevent and treat the dementia has been known for increasing the concentration of the neurotransmitter acetylcholine by inhibiting the activity of acetylcholinesterase (AChE) degrading the acetylcholine which plays a central role in central nervous transmit system. However, the tacrine is expensive and has serious hepatotoxicity. Donepezil does not have hepatotoxicity, but causes various side-effects such as nausea, anorexia, diarrhea, and etc. by stimulating the parasympathetic nerve.

Therefore, a new drug for treating dementia which can treat the causes of the disease and does not have the side-effects is still needed and has been researched actively. As a part of the research, there is an effort to continuously develop a drug for inhibiting the formation of β-amyloid.

*Monsonia* sp. belongs to the family, Geraniaceae and is used for improving the indigestion and intestinal bleeding, etc. in southern Africa (Burkill, The useful plants of west tropical Africa, Vol. 2, The Royal Botanic Gardens Kew, 1994). *Monsonia angustifolia* grows naturally in Africa, especially the whole of South Africa. *Monsonia angustifolia* has various uses for treating such as headache, anthrax, blackwater fever, diarrhea, ophthalmia, snakebite, hemorrhoids, stomach ulcer, indigestion, and varicose veins in Africa (Roberts, Indigenous healing plants, Southern Book Publishers, 1990, pp. 81-82). It is also recorded that *Monsonia angustifolia* is used for liver disorder in african folk remedy (Ichikawa, The database of traditional plant utilization in Africa Center for African area studies, Kyoto University, http://130.54.103.36/aflora.nsf), but there is no published research on it. Other than a patent disclosing the use of a plant extract which includes *Monsonia angustifolia* for treating erectile dysfunction and improving libido (Fouche, WO 2007138531), there is no scientific report on the medicinal use of *Monsonia angustifolia*.

SUMMARY OF THE INVENTION

The present inventors researched a new drug for treating dementia which can treat the causes of the disease and does not have the side-effects, and identified that extracts of *Monsonia* sp. such as *Monsonia angustifolia* have an effect of prevention and/or treatment on dementia, to complete the present invention.

In an embodiment, it is an object to provide a composition for preventing, treating, improving and/or ameliorating a condition associated with β-amyloid in brain, comprising at least one selected from the group consisting of extracts of *Monsonia* sp., and a dried product and a concentrated product thereof.

Another embodiment provides a food composition for preventing and/or improving dementia comprising of at least one selected from the group consisting of extracts of *Monsonia* sp., and a dried product and a concentrated product thereof.

Further embodiment provides a method of preparing an extract of *Monsonia* sp. having an optimized inhibitory effect on β-amyloid formation.

In another embodiment, it is to provide a method for inhibiting the formation of beta-amyloid using at least one selected from the group consisting of extracts of *Monsonia* sp., and a dried product and a concentrated product thereof.

In still another embodiment is to provide a method for preventing and/or treating dementia, ameliorating memory impairment and/or improving memory, comprising at least one selected from the group consisting of extracts of *Monsonia* sp., and a dried product and a concentrated product thereof.

In another embodiment, it is an object to provide a use of at least one selected from the group consisting of extracts of *Monsonia* sp., and a dried product and a concentrated product thereof for preventing and/or treating dementia, ameliorating memory impairment and/or improving memory.

Figure 4:
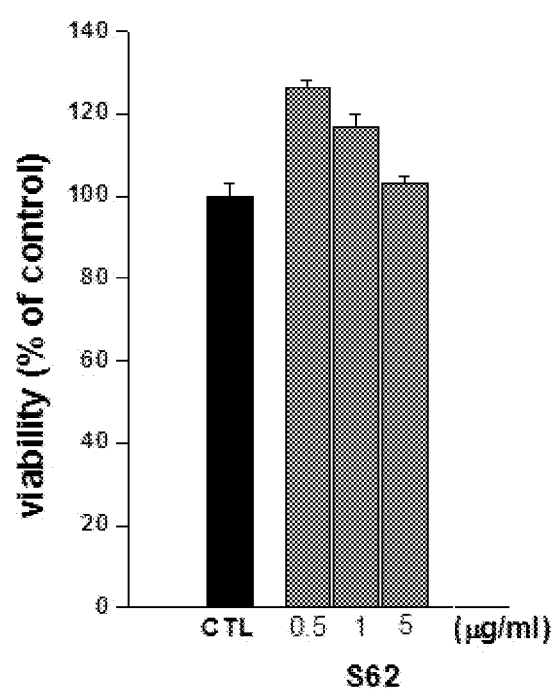

FIG. 4 is a graph showing that the added concentration of an extract of *Monsonia angustifolia* (S62) affects on cell death (CTL: negative control).

DETAILED DESCRIPTION OF THE INVENTION

The present inventors found that the plant extracts of *Monsonia* sp. such as *Monsonia angustifolia, Monsonia galpinii* and *Monsonia brevirostrata* have the activity of suppressing the formation of β-amyloid, among the extracts, the extract of *Monsonia angustifolia* has the most effective effect of suppressing β-amyloid formation, and the extract of *Monsonia brevirostrata* is also capable of suppressing the formation of β-amyloid, thereby presenting the use of the plant extracts of *Monsonia* sp. for prevention, improvement, and/or treatment of dementia.

The present invention provides a pharmaceutical composition for prevention and/or treatment of dementia which comprises at least one selected from the group consisting of plant extracts of *Monsonia* sp., and a dried product and a concentrated product thereof, as an active ingredient.

Another embodiment provides a method for inhibiting the formation of beta-amyloid comprising administering a therapeutically effective amount of a composition comprising at least one selected from the group consisting of extracts of *Monsonia* sp., and a dried product and a concentrated product thereof and pharmaceutically acceptable salts thereof, to a subject in need.

Still further embodiment provides a method for preventing, treating, improving and/or ameliorating a disease or condition associated with beta-amyloid in brain, for examples dementia, memory and/or memory impairment, comprising administering a therapeutically effective amount of a composition comprising at least one selected from the group consisting of extracts of *Monsonia* sp., and a dried product and a concentrated product thereof and pharmaceutically acceptable salts thereof, to a subject in need.

As used herein, the term "and/or," when used in a list of two or more items, means that any one of the listed items can be employed by itself, or any combination of two or more of the listed items can be employed.

It is to be understood that this invention is not limited to the particular methodology, protocols, animal species or genera, and reagents described, as such may vary. It is also to be understood that the terminology used herein is for the purpose of describing particular embodiments only, and is not intended to limit the scope of the present invention that will be limited only by the appended claims.

As used herein the term "subject", refers to an animal, preferably a mammal, and most preferably a human both male and female, who has been the object of treatment, observation or experiment.

The term "therapeutically effective amount" as used herein, means that amount of active composition or pharmaceutical agent that elicits the biological or medicinal response in a tissue system, animal or human that is being sought by a researcher, veterinarian, medical doctor or other clinician, which includes alleviation of one or more of the signs or symptoms of the disease or disorder being treated.

The term "pharmaceutically acceptable salts" shall mean non-toxic salts of the composition employed in this invention which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

The term "treating" or "treatment" as used herein, refers to any indicia of success in the prevention and/or treatment, amelioration of dementia, memory or memory impairment and modification of dementia, including any objective or subjective parameter such as abatement; remission; diminishing of memory or condition more tolerable to the patient; slowing in the rate of degeneration or decline or worsening of the illness; making the final point of worsening less debilitating; or improving a subject's physical or mental well-being. The treatment or amelioration of symptoms can be based on objective or subjective parameters; including the results of a physical examination, neurological examination, and/or psychiatric evaluations. Accordingly, the term "treating" or "treatment" includes the administration of the composition or agents of the present invention for treatment of any form of dementia in both males and females. In some instances, treatment with the composition of the present invention will done in combination with other composition to prevent, inhibit, or arrest the progression of the dementia.

The terms "subject" or "patient" are used herein interchangeably and mean any mammal including but not limited to human beings including a human patient or subject to which the compositions of the invention can be administered. The term mammals include human patients, both male and female and non-human primates, as well as experimental animals such as rabbits, rats, mice, and other animals.

An experimental embodiment confirmed that in the HeLa cell line transfected with the gene of amyloid precursor protein (APP), which was treated with an extract of one of *Monsonia* sp., e.g. *Monsonia angustifolia*, the formation of β-amyloid is effectively inhibited thereby (Experimental Example 1). Another experimental embodiment confirmed that in the HeLa cell line transfected with the gene of amyloid precursor protein, which was treated with an extract of another one of *Monsonia* sp., e.g. *Monsonia brevirostrata*, the formation of β-amyloid is also effectively inhibited thereby (Experimental Example 2).

Therefore, the plants of *Monsonia* sp., may include *Monsonia angustifolia, Monsonia galpinii, Monsonia brevirostrata* and the like, more specifically *Monsonia angustifolia* and/or *Monsonia brevirostrata*, and more preferably *Monsonia angustifolia*. The plants of *Monsonia* sp. may be grown naturally or cultivated. For example, the part of plant to be extracted may be root, whole plant including the root, and aboveground part except for the root, and the like, but may not be limited thereto.

The extract of *Monsonia* sp., can be obtained by extracting the plant with at least one solvent selected from the group consisting of water, a linear or branched alcohol having 1 to 4 carbon atoms, ethyl acetate, dichloromethane, and acetone.

In an experiment, the change in the inhibitory effect on the formation of β-amyloid was tested on the extracts of sample obtained from the wild *Monsonia* sp., cultivated *Monsonia* sp., and on the extracts of *Monsonia* sp. depending on extract solvents, as a result, both of the wild plant and the cultivated plant exhibited the highest inhibitory effect on the formation of β-amyloid in the case of an extract obtained by using a mixture of a linear or branched alcohol having 1 to 4 carbon atoms and dichloromethane at the volume ratio of 1:1 or an extract obtained by using a linear or branched alcohol having 1 to 4 carbon atoms, to optimize the solvent used for extraction (Experimental Example 3).

To achieve higher inhibitory effect on the formation of β-amyloid, the extract of *Monsonia* sp. can be extracted using a mixture of dichloromethane and a linear or branched alcohol having 1 to 4 carbon atoms (for example, methanol) at the volume ratio of 1:0.8 to 1.2 (volume of dichloromethane: volume of a linear or branched alcohol having 1 to 4 carbon atoms), or a linear or branched alcohol having 1 to 4 carbon atoms, and more preferably, the extract can be obtained using a mixture of methanol and dichloromethane at the volume ratio of 1:1, or ethanol.

In considering the extracting efficiency of the *Monsonia* sp., the solvent may be used at an amount of 1 to 50 times by volume, or preferably 10 to 30 times by volume, on the basis of the weight of the *Monsonia* sp. The extract time cannot be limited particularly and for example, can be 0.5 to 12 hours, or preferably 0.5 to 3 hour, to sufficiently extract the effective ingredients. The extract temperature cannot be limited particularly and for example, can be room temperature to below the boiling point of solvent to efficiently extract the effective ingredients.

The extraction can be performed by any conventional extracting method known to an ordinarily skilled person in the art. Specifically, the extracting method may include a cold-precipitation, a heating extraction, an ultrasound extraction, a filtration, a high pressure extract method, a reflux extraction, a super critical fluid extraction, an electrical extraction, and the like.

If desired, the method may further include the step of filtration, concentration and/or freezing-drying which are known to an ordinarily skilled person in the art. The dried product or the concentrated product of the extract refers to one concentrated or dried by the conventional method.

As used herein, the term, dementia, is intended to include a vascular dementia and Alzheimer's disease, and specifically, means Alzheimer's disease.

The amount of the extract of *Monsonia* sp., which is contained in the pharmaceutical composition of the present invention as an active ingredient, may be determined properly in consideration of usage type, usage object, condition of patient, kind and seriousness of disease, and the like. The amount of the extract of *Monsonia* sp. in the pharmaceutical composition may be 0.001 to 99.9 wt %, or preferably 0.1 to 50 wt %, on the basis of solid content, but is not limited thereto. The term "solid content" means a weight of the part which remains as residue after removing the solvent in the extracted product.

The pharmaceutical composition can be administered to a mammal including a human according to various routes of administration. The routes of administration can be any conventional route normally used to administer a medicament, and for example, the composition may be administered through oral, rectal, intravenous, intramuscular, intradermal, endometrial, or intracerebroventricular pathway. The pharmaceutical composition can be formulated according to the conventional formulating method in formulation of oral forms, such as powder, granule, tablet, capsule, suspension, emulsion, syrup, aerosol, and the like; paraenteral forms, such as transdermal, superpository, and the like; and sterile intravenous forms.

The pharmaceutical composition can further include pharmaceutically-applicable and physiologically-acceptable additives such as carriers, exipients and diluents as well as the extract of *Monsonia* sp. The carriers, exipients and diluents applicable to the pharmaceutical composition may include lactose, dextrose, sucrose, sorbitol, mannitol, xylitol, erythrytol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxylbenzoate, talc, magnesium stearate, mineral oil and the like. In the formulation of the composition, exipients and diluents used generally such as filling agent, extending agent, binding agent, wetting agent, disintegrating agent, surfactant, and the like can be added. The solid formulations for oral administration include tablet, pill, powder, granule, capsule and the like, and can be prepared by mixing the extract of *Monsonia* sp. with at least exipients such as starch, calcium carbonate, sucrose, lactose, gelatin and the like. Besides simple exipients, the lubricants such as magnesium stearate, talc and the like can be added. In a liquid solution for oral administration including suspension, solution, emulsion, syrup and the like, various exipients such as wetting agent, sweetening agent, flavoring agent, preserving agent and the like can be used, as well as simple diluents including water, liquid, paraffin and the like. The formulations for paraenteral administration include sterile aqueous solution, non-aqueous solvent, suspending agent, emulsifying agent, freeze-drying agent, suppository and transdermal agent. The suspending agent and non-aqueous solvent include propylene glycol, polyethylene glycol, plant oil such as olive oil, injectable ester such as ethyl oleate, and the like. The base material for suppository can be witepsol, macrogol, tween 61, cacao oil, laurin oil, glycerol gelatin and the like.

The pharmaceutical composition can be administered to a human alone or in combination of pharmaceutically-acceptable diluents which are selected on the basis of the administration route and standard pharmaceutical practice. For examples, the composition can be formulated as a tablet containing an active ingredient together with starch or lactose, a capsule containing an active ingredient alone or in combination of exipient, an elixir or suspension including a flavoring agent or a coloring agent, to be administered orally, intraorally, or sublingual. The liquid solution can be formulated together with pharmaceutically-acceptable additives such as a suspending agent (for example, semi-synthetic glyceride including methyl cellulose and witepsol, a mixture of apricot kernel oil and PEG-6 ester, or a mixture of PEG-8 and caprylic/capric glyceride).

Another embodiment provides a food composition for preventing and/or improving dementias comprising at least one selected from the group consisting of extracts of *Monsonia* sp., a dried product of the extracts, and a concentrated product of the extracts.

Hereinafter, the term, food refers to natural or artificial product containing at least one nutrient, and generally includes various foods, health functional food, beverage, food additives, and beverage additives. The food composition means a combination of the materials to be used for various foods. The examples of food include foods, beverages, gums, teas, functional food and the like. Also, the food for special dietary uses such as formulated meat and infant and baby food, processed meat product, processed fish product, tofu, gellied food, noodles such as ramen and noodle, dietary supplement, snacks, other processed food, beverage, health functional beverage such as a food for relieving hangovers, and other dietary supplements, but not limited thereto. The health functional food, beverage, food additive or beverage additive can be prepared according to the convention method to make them.

The quantity of the extract of *Monsonia* sp. as an active ingredient in the food composition can be determined in consideration of usage type, object, etc, and for examples be 0.00001 to 99.9 wt %, and preferably 0.001 to 50 wt % on the basis of solid content.

Further embodiment of the present invention provides a method of preparing an extract of *Monsonia* sp. having an excellent inhibitory effect on the β-amyloid formation.

The method may comprise the steps of:

1) providing at least one plant of *Monsonia* sp. selected from the group consisting of *Monsonia angustifolia* and *Monsonia brevirostrata*; and 2) extracting the provided plant by adding at least one solvent selected from the group consisting of water, a linear or branched alcohol having 1 to 4 carbon atoms, ethyl acetate, dichloromethane, and acetone.

Step 1) of providing the plant of *Monsonia* sp. may include the step of drying the plant of *Monsonia* sp.

Step 2) of extracting the plant can be carried out by adding a mixture of dichloromethane and a linear or branched alcohol having 1 to 4 carbon atoms (for example, methanol) at the volume ratio of 1:0.8 to 1.2, for example about 1:1, or a linear or branched alcohol having 1 to 4 carbon atoms (for example, ethanol), to the provided (e.g., dried) plant.

The extracting step can be once, or can be at least two times, for examples two or three times and the filtrates obtained in each step are mixed to produce the extract of *Monsonia* sp.

For example, the extracting step 2) may include the steps of:

2-1) obtaining a residue and a filtrate by firstly extracting the dried *Monsonia* sp. with a mixture of dichloromethane and a linear or branched alcohol having 1 to 4 carbon atoms at a volume ratio of 1:0.8 to 1.2 or a linear or branched alcohol having 1 to 4 carbon atoms, and filtrating;

2-2) obtaining a filtrate by secondly extracting the residue obtained from step 2-1) with a mixture of dichloromethane and a linear or branched alcohol having 1 to 4 carbon atoms at a volume ratio of 1:0.8 to 1.2 or a linear or branched alcohol having 1 to 4 carbon atoms and filtrating; and 2-3) mixing the filtrate obtained from step 2-1) and the filtrate obtained from step 2-2).

In another embodiment, the extracting step 2) may include the steps of:

2-1') obtaining a residue and a filtrate by firstly extracting the dried *Monsonia* sp. with a mixture of dichloromethane and a methanol at the volume ratio of 1:1 or ethanol, and filtrating;

2-2') obtaining a filtrate by secondly extracting the residue obtained from step 2-1) with a mixture of dichloromethane and a methanol at the volume ratio of 1:1 or ethanol, and filtrating; and 2-3') mixing the filtrate obtained from step 2-1) and the filtrate obtained from step 2-2).

The provided plant of *Monsonia* sp. can be root, whole plant including root, or aboveground part without root.

The amount of extracting solvent, the extracting time, and the extracting temperature are the same as described above.

As described above, the extract of *Monsonia* sp. can inhibit the formation of β-amyloid which has been known as a causing factor of dementia, specifically Alzheimer's disease, and thus be used effectively for preventing or treating dementia.

EXAMPLES

The present invention will be further described in more detailed with reference to the following examples. These examples, however, should not be interpreted as limiting the scope of the invention in any manner.

Example 1

Preparation of an Extract of *Monsonia angustifolia*

*Monsonia angustifolia* grown naturally or cultivated in Pretoria of South Africa was collected on January through February, 2011, and used for the test. Reference sample of No. 39250002 is preserved at herbarium of South African Biodiversity Institute.

Whole plant of *Monsonia angustifolia* was dried, cut finely, and 266 g cut plant was put into an extractor. In the extractor, 6 L of a mixed solvent of methanol and dichloromethane at the mixing ratio of 1:1 (v/v) was added to, extracted for 1 hour at a room temperature with stirring and then filtrated. The residue was added with 6 L of a mixed solvent of methanol and dichloromethane at the mixing ratio of 1:1 (v/v), extracted secondly for 1 hour, and filtrated to obtain a filtrate. The solution was mixed with primary-filtrated solution. After filtrating the mixture, the produced solution was concentrated in a concentrator under a reduced pressure at 40° C., until the solvent was completely removed, to obtain 27.3 g extract of *Monsonia angustifolia* (S62) (Yield: 10.3%).

Example 2

Preparation for Extracts of *Monsonia galpinii* and *Monsonia brevirostrata*

*Monsonia galpinii* and *Monsonia brevirostrate* grown naturally in Pretoria of South Africa was collected and used for the test.

*Monsonia galpinii* was divided into an aboveground part and an underground part, and each part was cut finely. According to the substantially same method of Example 1, the extracts of aboveground part (S85) and an underground part (S86) were obtained.

Whole plant of *Monsonia brevirostrata* was dried and cut finely, and treated according to the substantially same method of Example 1 to produce an extract of *Monsonia brevirostrata* (S87).

Example 3

Preparation for Extracts of *Monsonia angustifolia* by Using Different Solvents

Whole plants of *Monsonia angustifolia* cultured and *Monsonia angustifolia* grown wild in Pretoria of South Africa were collected on August, 2011, dried and cut finely. The cut products were added with ethanol, water or a mixture of dichloromethane and methanol at the volume ratio of 1:1 and extracted according to the substantially same method of Example 1 to obtain an extract of wild *Monsonia angustifolia* with a mixture of dichloromethane and methanol at a ratio of 1:1 (v/v) (S90), an extract of wild *Monsonia angustifolia* with water (S96), an extract of wild *Monsonia angustifolia* with ethanol (S97), an extract of cultivated *Monsonia angustifolia* with ethanol (S93), an extract of cultivated *Monsonia angustifolia* with water (S94) and an extract of cultivated *Monsonia angustifolia* with a mixture of dichloromethane and methanol at a ratio of 1:1 (v/v) (S95).

Experimental Example 1

Inhibitory Effect of *Monsonia angustifolia* Extract on the Formation of β-Amyloid In order to test whether the *Monsonia angustifolia* extract (S62) obtained in Example 1 inhibits the formation of β-amyloid, the HeLa cell line was transfected with the gene of amyloid precursor protein derived from human and cultured in DMEM culture medium (Cat. #11995, Gibco, USA). The cell line was donated by Prof. Tae-Wan Kim in Department of Pathology, Columbia University Medical Center, New York, N.Y. 10032, USA.

Figure 1:
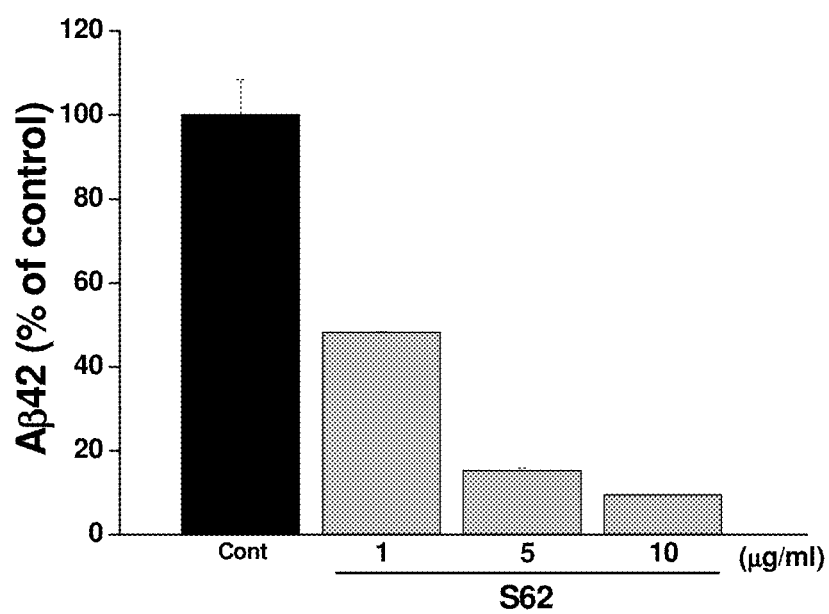
FIG. 1 is a graph showing the inhibitory effect of *Monsonia angustifolia* extract (S62) in Example 1 depending on the concentration of the added extract on the formation of β-amyloid (Aβ42) (Cont: negative control).

Specifically, the *Monsonia angustifolia* extract (S62) obtained in Example 1 was added to the cell culture solution at an amount indicated in FIG. 1, and cultured for 8 hours at 37° C. The amount of β-amyloid secreted to the cell culture solution was measured. Aβ42 among two kinds of β-amyloid was quantified with Human β-Amyloid [1-42](Aβ42) Colorimetric ELISA kit (#KHB3442; BioSource International, Inc., U.S.A.).

The measured amounts of β-amyloid were shown in FIG. 1. The negative control was the culture without treatment of *Monsonia angustifolia* extract. As shown in FIG. 1, the inhibition on the formation of Aβ42 was dependent upon the concentration of *Monsonia angustifolia* extract.

Experimental Example 2

Figure 2:
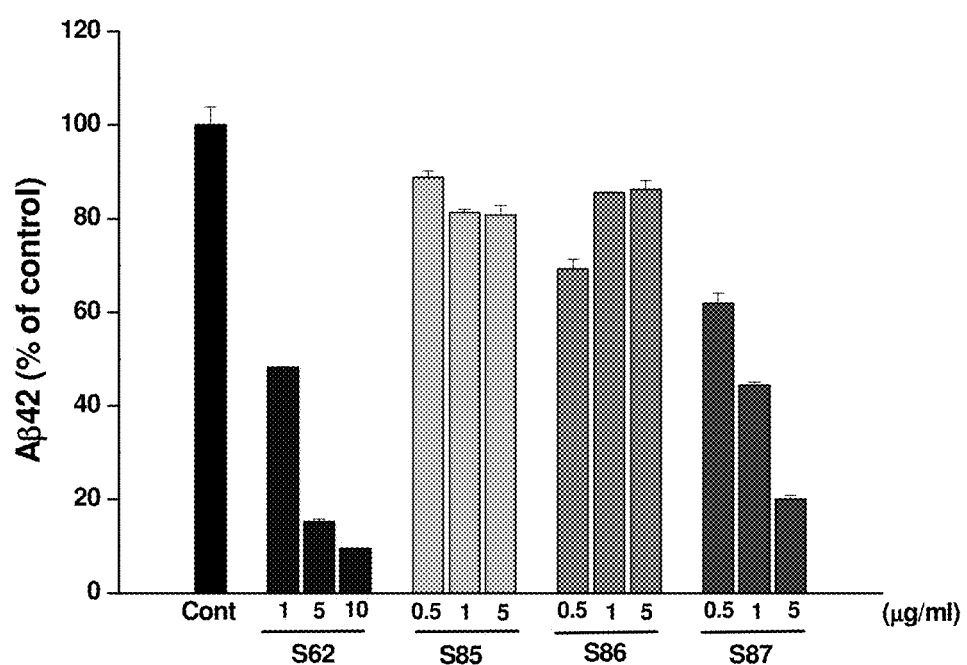
FIG. 2 is a graph showing the inhibitory effect of the extracts of aboveground plant part (S85) and underground part (S86) of *Monsonia galpinii*, and of whole plant extract of *Monsonia brevirostrata* (S87) in Example 2 on the formation of β-amyloid (Cont: negative control, S62: positive control).

Inhibitory Effect of *Monsonia galpinii* and *Monsonia brevirostrata* on the Formation of β-Amyloid In order to test the inhibitory effect of the aboveground part extract (S85) and the underground part extract (S86) of *Monsonia galpinii* and whole plant extract_(S87) of *Monsonia brevirostrate* on the formation of β-amyloid, the extracts were added to the cell culture solution at an concentration indicated in FIG. 2, and the amount of produced β-amyloid (Aβ42) was measured according to the method of Test Example 1. β-amyloid (Aβ42) was quantified with Human β-Amyloid [1-42] (Aβ42) Colorimetric ELISA kit (#KHB3442; BioSource International, Inc., U.S.A.).

The measured amounts of β-amyloid were shown in FIG. 2. The culture without treatment of *Monsonia angustifolia* extract was used as a negative control. The test result of the extract_(S62) of *Monsonia angustifolia* obtained by using a mixture of dichloromethane and methanol at a ratio of 1:1 (v/v) was shown together in FIG. 2 to compare the effects of extracts S85, S86 and S87. As shown in FIG. 2, the inhibition on the formation of Aβ42 was dependent upon the concentration of the whole plant extract of *Monsonia brevirostrata* (S87), and was excellent compared to those of aboveground part extract and underground part extract of *Monsonia galpinii*.

Experimental Example 3

Figure 3:
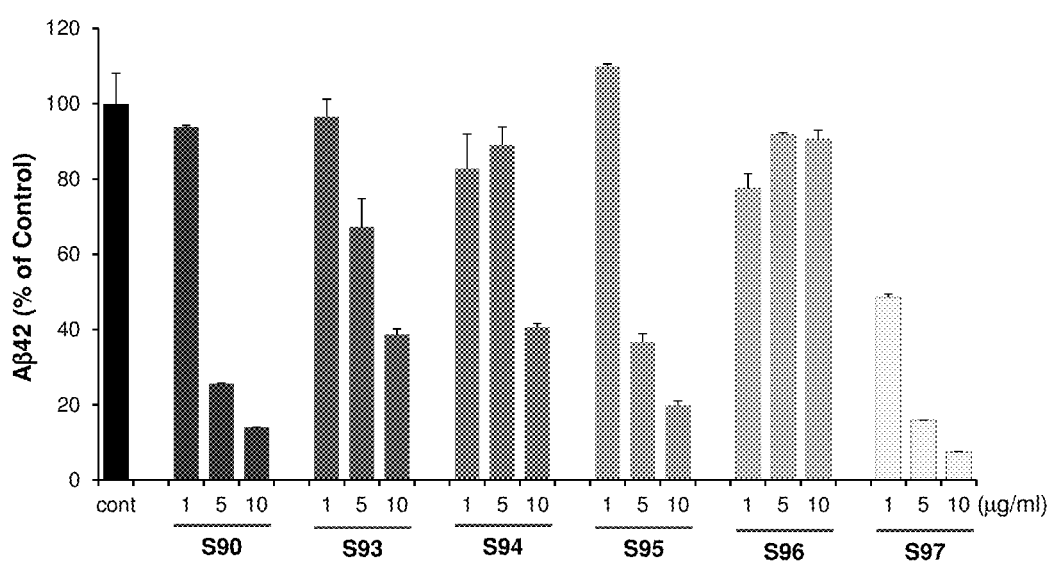
FIG. 3 is a graph showing the inhibitory effect of an extract obtained by extracting wild *Monsonia angustifolia* whole plant with a mixture of dichloromethane and methanol at the volume ratio of 1:1 (S90), an extract obtained by extracting wild *Monsonia angustifolia* whole plant with water (S96), an extract obtained by extracting wild *Monsonia angustifolia* whole plant with ethanol (S97), an extract obtained by extracting cultivated *Monsonia angustifolia* whole plant with aqueous ethanol solution (S93), an extract obtained by extracting cultivated *Monsonia angustifolia* whole plant with water (S94), and an extract obtained by extracting wild *Monsonia angustifolia* whole plant with a mixture of dichloromethane and methanol at the volume ratio of 1:1(S95) in Example 3 on the formation of β-amyloid (Cont: negative control).

Inhibitory Effect of the Extracts Obtained from *Monsonia angustifolia* on Using Various Solvents on the Formation of β-Amyloid In order to test the inhibitory effects of an extract obtained by extracting wild *Monsonia angustifolia* whole plant with a mixture of dichloromethane and methanol at ratio of 1:1 (S90), an extract obtained by extracting wild *Monsonia angustifolia* whole plant with water (S96), an extract obtained by extracting wild *Monsonia angustifolia* whole plant with ethanol (S97), an extract obtained by extracting cultivated *Monsonia angustifolia* whole plant with aqueous ethanol solution (S93), an extract obtained by extracting cultivated *Monsonia angustifolia* whole plant with water (S94), and an extract obtained by extracting wild *Monsonia angustifolia* whole plant with a mixture of dichloromethane and methanol at ratio of 1:1 (S95) in Example 3 on formation of β-amyloid, the extracts were added to the cell culture solution at an concentration indicated in FIG. 3, and the amount of produced β-amyloid (Aβ42) was measured according to the method of Test Example 1. β-amyloid (Aβ42) was quantified with Human β-Amyloid [1-42](Aβ42) Colorimetric ELISA kit (#KHB3442; BioSource International, Inc., U.S.A.).

The measured amounts of β-amyloid were shown in FIG. 2. The culture without treatment of *Monsonia angustifolia* extract was used as a negative control. As shown in FIG. 3, an extract obtained by extracting wild *Monsonia angustifolia* whole plant with a mixture of dichloromethane and methanol at ratio of 1:1 (S90), an extract obtained by extracting wild *Monsonia angustifolia* whole plant with a mixture of dichloromethane and methanol at ratio of 1:1 (S95), and an extract obtained by extracting wild *Monsonia angustifolia* whole plant with ethanol (S97) represented excellent inhibition effect. In addition, an extract obtained by extracting cultivated *Monsonia angustifolia* whole plant with water (S94) showed an inhibitory effect on the formation of β-amyloid (Aβ42) at a concentration of 10 μg/ml.

Experimental Example 4

The Effect of *Monsonia angustifolia* Extract on the Cell Death and Safety Test

To test the effect of *Monsonia angustifolia* extract on the cell death, the known MTT Cell Proliferation assay method (ATCC catalog #30-1010K, Manassas, USA) was used. Specifically, HeLa cells were treated with various concentration of *Monsonia angustifolia* extract (S62) for 8 hours (see Test Example 1), the viable cell was quantified, and the result was shown in FIG. 4. The culture without treatment of *Monsonia angustifolia* extract was used as a negative control.

As shown in FIG. 4, the cell death was not observed even at the treatment of 5 μg/ml of the *Monsonia angustifolia* extract (S62).

Therefore, the fact that the *Monsonia angustifolia* extract could inhibit the formation of β-amyloid (Aβ42) was not simply based on the cell death. The *Monsonia angustifolia* extract showed low cytotoxicity within the concentration inhibiting the formation of β-amyloid, and thus can be safely used as a pharmaceutical composition and a food composition.

What is claimed is:

1. A method for treating, improving and/or ameliorating a condition associated with β-amyloid in the brain of a human in need thereof, comprising the steps of:
    extracting *Monsonia angustifolia* or *Monsonia brevirostrate* with at least a solvent selected from the group consisting of water, a linear or branched alcohol having 1 to 4 carbon atoms, ethyl acetate, dichloromethane, and acetone to obtain a composition comprising an extract of *Monsonia angustifolia* or *Monsonia brevirostrate*, and administering to said human in need thereof a therapeutically effective amount of the *Monsonia angustifolia* or

*Monsonia brevirostrate* extract to effectively treat, improve and/or ameliorate a condition associated with β-amyloid in the brain of a human in need thereof, wherein the condition associated with β-amyloid in the brain of a human in need thereof is selected from the group consisting of dementia and Alzheimer's disease.

2. The method according to claim 1, wherein the extract is dried.

3. The method according to claim 1, wherein the extract is concentrated.

4. The method according to claim 1, wherein the extract inhibits formation of the β-amyloid by increasing APP-α production.

5. The method according to claim 1, wherein the extract is obtained by extracting with a mixed solvent of dichloromethane and a linear or branched alcohol having 1 to 4 atoms at a volume ratio of 1:0.8 to 1.2 (v/v).

6. The method according to claim 1, wherein the extract is obtained by extracting at least one solvent selected from the group consisting of water and a linear or branched alcohol having 1 to 4 carbon atoms.

7. The method according to claim 1, wherein the alcohol is methanol or ethanol.

8. The method according to claim 1, wherein the extract is administered orally, rectally, intravenously, intramuscularly, intradermally, endometrially, or intracerebroventricularly.

9. The method according to claim 1, further comprising: adding to the composition a physiologically-acceptable additive.

10. The method according to claim 1, further comprising: adding to the composition a physiologically-acceptable diluent.

* * * * *